(12) United States Patent
Shibuya et al.

(10) Patent No.: US 8,916,095 B2
(45) Date of Patent: Dec. 23, 2014

(54) AUTOMATIC ANALYZER

(75) Inventors: Satoshi Shibuya, Hitachinaka (JP); Kazuhiro Nakamura, Naka (JP)

(73) Assignee: Hitachi High-Technologies Corporation, Tokyo (JP)

(*) Notice: Subject to any disclaimer, the term of this patent is extended or adjusted under 35 U.S.C. 154(b) by 545 days.

(21) Appl. No.: 12/326,227

(22) Filed: Dec. 2, 2008

(65) Prior Publication Data

US 2009/0142231 A1 Jun. 4, 2009

(30) Foreign Application Priority Data

Dec. 3, 2007 (JP) .................................. 2007-311884

(51) Int. Cl.
*G01N 21/00* (2006.01)
*G01N 35/00* (2006.01)

(52) U.S. Cl.
CPC .... *G01N 35/00663* (2013.01); *G01N 35/00594* (2013.01); *G01N 35/00693* (2013.01); *G01N 2035/00673* (2013.01)
USPC .......................................................... 422/64

(58) Field of Classification Search
CPC ..... G01N 21/13; G01N 33/48; G01N 33/483; G01N 33/50; G01N 35/00584; G01N 35/00594; G01N 35/00693; G01N 35/00712; G01N 3/62; G01N 21/00; B01J 19/00; B01J 2219/0054; B01J 2219/00689
USPC ........................................................... 422/64
See application file for complete search history.

(56) References Cited

U.S. PATENT DOCUMENTS

| | | | | |
|---|---|---|---|---|
| 5,424,212 A | * | 6/1995 | Pinsl-Ober et al. | 436/50 |
| 6,019,945 A | * | 2/2000 | Ohishi et al. | 422/65 |
| 6,080,364 A | * | 6/2000 | Mimura et al. | 422/67 |
| 7,150,857 B2 | * | 12/2006 | Hiramatsu et al. | 422/68.1 |

FOREIGN PATENT DOCUMENTS

| | | |
|---|---|---|
| JP | 8-262029 | 10/1996 |
| JP | 9-127122 A | 5/1997 |
| JP | 9-325150 | 12/1997 |
| JP | 2002-48800 A | 2/2002 |
| JP | 2003-66049 A | 3/2003 |
| JP | 2003-315343 A | 11/2003 |
| JP | 2003-315345 A | 11/2003 |
| JP | 2007-285920 A | 11/2007 |

* cited by examiner

*Primary Examiner* — Lore Jarrett
(74) *Attorney, Agent, or Firm* — Mattingly & Malur, PC

(57) ABSTRACT

The automatic analyzer stores: a predetermined period from the opening of a reagent vessel to the deterioration of the reagent; a reagent production lot number, reagent vessel unsealing time, and reagent expiration date as reagent information kept on a reagent-set-by-set basis; and relevant calibration curve factor information. The automatic analyzer judges whether a calibration curve factor for a reagent set is applicable or not to another reagent set of the analyzer with the same production number based on the predetermined period from the reagent vessel unsealing time and on the reagent expiration date.

9 Claims, 5 Drawing Sheets

FIG.3

CALIBRATION CURVE FACTOR INFORMATION

| ITEM NAME | REAGENT Pos | REAGENT Lot | FACTOR A | FACTOR B | FACTOR C | FACTOR D | EXTERNAL INPUT |
|---|---|---|---|---|---|---|---|
| Test1 | 5 | 00000001 | 123 | 4567 | — | — | * |
| Test1 | 6 | 00000001 | 123 | 4567 | — | — | |
| Test1 | 7 | 00000002 | 90 | 1020 | — | — | * |
| Test2 | 10 | 00000100 | 10.2 | 500 | 20.0 | 32.5 | |
| ... | ... | ... | ... | ... | ... | ... | ... |

CANCEL  REGISTER

AUTOMATIC ANALYZER

CROSS REFERENCE

The present application claims priority from Japanese application JP2007-311884 filed on Dec. 3, 2007, the content of which is hereby incorporated by reference into this application.

BACKGROUND OF THE INVENTION

1. Field of the Invention

The present invention relates to an automatic analyzer for performing qualitative/quantitative analysis of a biological sample such as blood and urine, and more particularly to an automatic analyzer that performs calculation by use of a calibration curve to obtain the result of analysis.

2. Description of the Related Art

Automatic analyzers for analyzing a biological sample such as blood and urine usually perform qualitative/quantitative analysis of a specific constituent contained in the sample by use of a reagent that reacts with the specific constituent. In particular, when the quantitative analysis is performed, in order to ensure the quantifiability, it is necessary to determine, as a calibration curve, the relationship between the absorbance, the emission intensity, or the turbidity, which is measured by the automatic analyzer, and the concentration by use of a sample whose concentration is known (this sample is called, for example, a "standard sample"). If a calibration curve is a straight line, the calibration curve is identified by a tilt and a y-intercept. Information used to identify such a calibration curve is designated as a "calibration curve factor". When analysis is performed using an automatic analyzer, a calibration curve factor is determined by use of a standard sample before a general sample (patient sample) is analyzed.

There are several kinds of analysis methods including: analyzing one analysis item by use of only one reagent (analysis with one reagent); analyzing one analysis item by use of two kinds of reagents (analysis with two reagents); and analyzing one analysis item by use of three or more kinds of reagents. When one analysis item is analyzed by use of two or more kinds of reagents, a calibration curve is created for each set of reagent bottles (reagent set) used for the analysis.

As a reagent set management method, there are two kinds of methods: attaching, to each reagent bottle, an ID such as a bar code describing reagent information (a reagent code, a reagent production lot number, a reagent sequence number, the reagent expiration date, and the like) to manage reagent sets; and handling a set of reagent bottles as one cassette, and attaching, to each cassette, an ID such as a bar code describing reagent information to manage reagent sets.

The difference in reaction characteristics on a production lot basis and the change in reagent characteristics due to the time elapsed cause a difference in the result of measurement between reagents used for one analysis item. Accordingly, when a reagent whose production lot differs is newly registered in the automatic analyzer, or as time progresses, it is necessary to perform calibration again, and then to regenerate a calibration curve in a current reagent state.

For the difference in reaction characteristics on a reagent production lot basis, JP-A-08-262029 discloses an automatic analyzer that holds analysis conditions in a reagent bar code on a reagent lot basis so as to eliminate the difference in reaction characteristics between reagent production lots, and that is capable of performing correct sample analysis without key inputting.

For the deterioration of a reagent due to the time elapsed, JP-A-09-325150 discloses an automatic analyzer that corrects a change in the result of measurement due to the deterioration of a reagent, and a change in characteristics with time, at the time of calibration and measurement.

On the other hand, some conventional automatic analyzers have a function of enabling a user to directly input a calibration curve factor from a screen, or the like. For example, this function is used when an operator has no standard solution in hand, or when the operator directly inputs a calibration curve factor provided by a reagent manufacturer because a standard solution is expensive. In another case, this function is used when a calibration curve factor is corrected because characteristics of a reagent have changed. After the calibration curve factor is inputted, an accuracy control sample is analyzed to check the validity of the calibration curve factor. The validated calibration curve factor is used for measurement of a sample.

In this case, even in a state in which a plurality of reagent sets are placed in the automatic analyzer for the purpose of analyzing one analysis item, because the difference between reagent lots and the change in reagent characteristics cause the difference as described above, a calibration curve factor is always inputted on a reagent set basis, and the calibration curve factor is applied to only an appropriate reagent set, which is the actual situation.

SUMMARY OF THE INVENTION

In the case of the conventional automatic analyzers, if a plurality of reagent sets are placed in the automatic analyzer for the purpose of analyzing one analysis item, it is basically necessary to create a calibration curve factor on a reagent set basis, which puts a heavy load on an operator.

However, if a calibration curve factor created for one reagent set is applied to all of the other reagent sets belonging to the same analysis item, which are placed in the automatic analyzer, the difference in reagent production lot number and the change in characteristics of the reagents will cause reaction characteristics to differ. Accordingly, there is a higher possibility that the reliability of the result data will decrease.

An object of the present invention is to provide an automatic analyzer that is capable of reducing the time and effort spent on measurement of a calibration curve factor with the reliability of measurement data kept high, the measurement being conventionally made on a reagent set basis.

In order to achieve the above-described object, according to one aspect of the present invention, there is provided an automatic analyzer that is configured as follows:

An automatic analyzer comprising:

storage means for storing on a reagent-by-reagent basis calibration curve information and the result of judgment as to whether or not a reagent is effective, wherein said automatic analyzer further comprises means for storing the calibration curve information of a reagent, the means storing, when a reagent is newly provided for the automatic analyzer, if the calibration curve information of the same reagent as the newly provided reagent has already been stored in the storage means, and if the expiration date of the reagent whose calibration curve information has already been stored is not yet reached, the calibration curve information of the reagent which has already been stored in the storage means as the calibration curve information of the newly provided reagent.

A more preferable configuration will be described as below.

The following information is stored: the predetermined specified time from a point of time at which a reagent is opened until characteristics of the reagent change; a reagent production lot number, reagent unsealing time, reagent expiration date, which are reagent information to be managed on a reagent set basis; and related calibration curve factor information.

When a calibration curve factor is created for a certain reagent set, a judgment is made from the reagent unsealing time, the predetermined specified time, and the expiration date of the reagent as to whether or not reagent characteristics have changed. If it is judged that the reagent characteristics have not changed, the other reagent sets placed in the automatic analyzer are also subjected to the same judgment processing under the same conditions. If a reagent set whose production lot number is the same as that of the reagent set for which the calibration curve factor has been created is found, the other reagent sets are regarded as homogeneous reagents, and accordingly, the calibration curve factor is applied to the other reagent sets.

The change in reagent characteristics may be divided into a plurality of stages in response to the time (in particular, in a case where a reagent whose expiration date is long is used). In this case, the change in reagent characteristics may also be divided into not only two stages (reagent characteristics have changed, or have not changed) but also a plurality of stages in response to the elapsed time. For example, calibration curve information is stored in groups of one day after the opening, two days after the opening, and the like, beforehand. Calibration curve information belonging to a group whose elapsed time after the opening corresponds to that of the placed reagent is applied. In addition, depending on facilities such as a hospital, the following operation is required: for some kinds of reagents, always recreating a calibration curve instead of applying a stored calibration curve of another reagent. Therefore, it may also be so configured that a kind of reagent whose calibration curve information is applied, and a kind of reagent whose calibration curve information is not applied, are registered beforehand.

According to the present invention, the time and effort required to create a calibration curve factor on a reagent set basis can be reduced with the reliability of measurement data kept high. This makes it possible to reduce the labor of an operator, and to save the cost of the expensive standard solution.

BRIEF DESCRIPTION OF THE DRAWINGS

FIG. 3 is a diagram illustrating a calibration curve factor input/display screen;

DESCRIPTION OF THE PREFERRED EMBODIMENT

Figure 1:
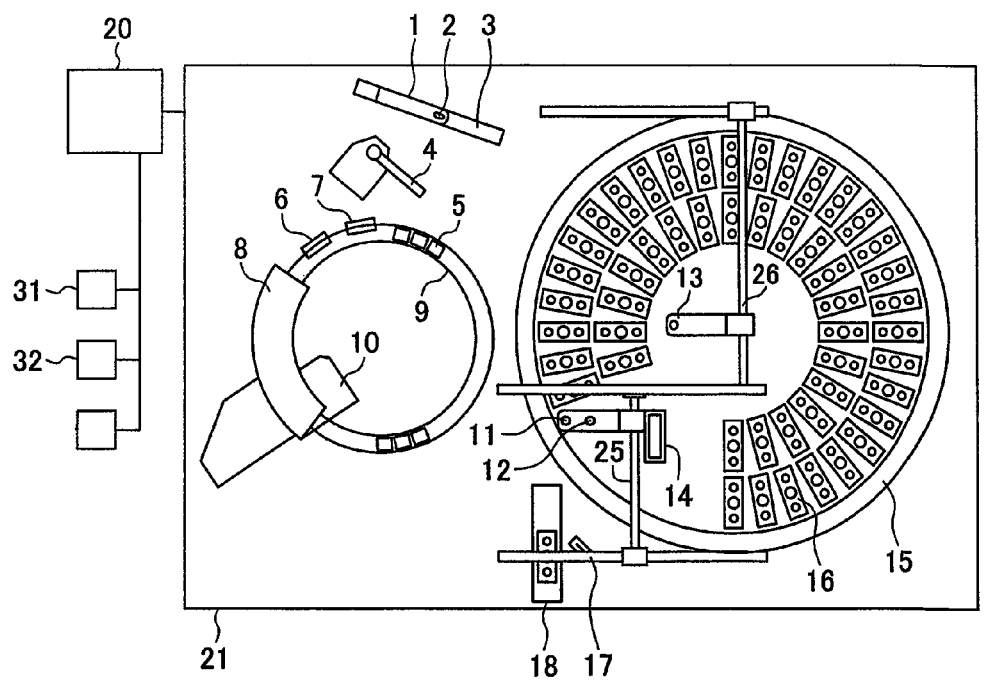
FIG. 1 is a diagram illustrating an overall configuration of an automatic analyzer according to one embodiment of the present invention.

A preferred embodiment of the present invention is described below with reference to the accompanying drawings. FIG. 1 is a top view illustrating the embodiment of the invention.

The embodiment is described as a method in which one set of reagent vessels (bottles) are handled using one cassette.

Reaction vessels 5 are circumferentially disposed on a reaction disk 9 placed on a chassis 21.

A plurality of reagent cassettes 16 can be circumferentially placed on a reagent disk 15. One reagent cassette 16 can accommodate three kinds of reagents (first, second, and third reagents) at the maximum.

A transfer mechanism 3 is disposed at a position close to the reaction disk 9. The transfer mechanism 3 is used to move a rack 1 on which a sample vessel 2 is placed. Rails 25 and 26 are disposed above the reagent disk 15. The rail 25 is provided with a reagent dispensing probe 11, a reagent vessel opening mechanism 12, and a reagent cassette transfer mechanism 14, all capable of moving in three axial directions with the rail 25. The rail 26 is provided with a reagent dispensing probe 13.

The reagent dispensing probes 11 and 13 are connected to a reagent pump, not shown in the figure.

A sample dispensing probe 4 is disposed between the reaction vessels 5 and the transfer mechanism 3. The sample dispensing probe 4 is capable of rotating and moving up and down. The sample dispensing probe 4 is connected to a sample pump, not shown in the figure. Components disposed around the reaction disk 9 include stirring devices 6 and 7; an optical detection device 10 having a light source; and a vessel rinsing mechanism 8. The vessel rinsing mechanism 8 is connected to a rinsing pump, not shown in the figure.

Connections are made between a controller 20 and each of the following components: the sample pump, the reagent pump, and the rinsing pump (all not shown); the optical detection device 10 having a light source; the reaction disk 9; the reagent disk 15; the reagent dispensing probes 11 and 13; and the sample dispensing probe 4.

The transfer mechanism 3 transfers the rack 1 holding the sample vessel 2 containing a sample so that the sample is positioned at a sample suctioning position. The sample dispensing probe 4 suctions the sample at the sample suctioning position. Then, at a sample dispensing position, the sample dispensing probe 4 dispenses the sample into one of the reaction vessels 5 placed on the reaction disk 9. The rotation of the reaction disk 9 causes the reaction vessel 5 into which the sample has been dispensed to move to a first-reagent dispensing position, where the first reagent dispensing probe 11 dispenses into that reaction vessel 5 a first reagent contained in one of the reagent cassettes 16 held by the reagent disk 15. Next, the reaction vessel 5 into which the first reagent has been dispensed is moved to a stirring position, where the stirring device 6 stirs the first reagent and the sample.

If the addition of a second reagent is required, the reaction vessel 5 which has completed the stirring processing is moved to a second-reagent dispensing position. Then, at the second-reagent dispensing position, the second reagent dispensing probe 13 dispenses into the reaction vessel 5 a second reagent contained in the same reagent cassette 16 as above, which is placed on the reagent disk 15. The reaction vessel 5 which has completed the dispensing processing is moved to a stirring position, where the stirring device 7 stirs the sample and the first and second reagents in the reaction vessel 5 to cause them to fully react with one another.

The reaction vessel 5 containing the fully reacted sample is moved to an analysis position. The optical detection device 10 then measures the multiple-wavelength absorbance of the reacted sample at the analysis position, whereby a biochemical property of the reacted sample is analyzed.

Figure 2:
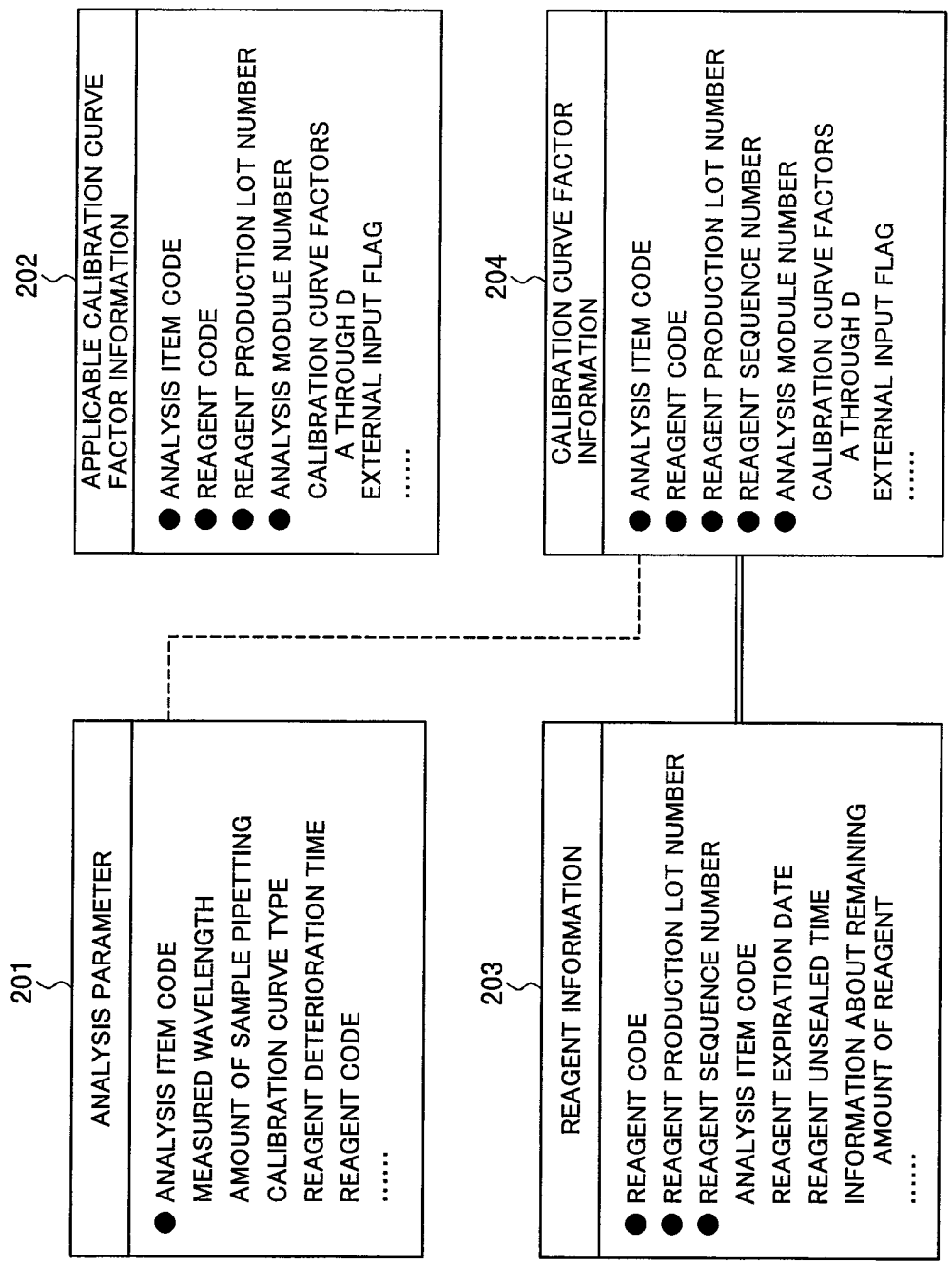
FIG. 2 is a diagram illustrating tables relating to calibration curve factors.

An operation unit 31 is constituted of a keyboard, a CRT, and the like. The CRT is used to display information about calibration curve factors, and the keyboard to input calibration curve factors. A storage unit 32 is formed of, for example, a hard disk drive. The storage unit 32 stores analysis parameters 201, reagent information 203, calibration curve factor information 204, and applicable calibration curve factor information 202, all of which are shown in FIG. 2.

The analysis parameters 201 are managed on an analysis item basis. The analysis parameters 201 include: an item code that is assigned to each analysis item; a calibration method; a reagent effective period from the unsealing of a reagent vessel until the deterioration of the reagent; and a reagent code of a reagent cassette used for an analysis item.

The automatic analyzer may have one such reagent effective period for all the reagents. Alternatively, it may also have reagent effective periods for respective reagents by setting those periods in their respective reagent barcode information.

The reagent information 203 is information about each reagent registered in the automatic analyzer. The reagent information 203 includes a reagent code, a reagent production lot number, a reagent sequence number, a reagent expiration date, reagent unsealing time, an analysis item code, and remaining amount information.

The calibration curve factor information 204 includes an analysis item code, a reagent code, a reagent production lot number, a reagent sequence number, a calibration curve factor, and an external input flag. The calibration curve factor information 204 is correlated with the reagent information 203. The applicable calibration curve factor information 202 is managed by using an analysis item code, a reagent code, and a reagent production lot number as keys. The applicable calibration curve factor information 202 includes: a calibration curve factor that can be applied to other reagents; and an external input flag that indicates the calibration factor has been input externally.

Standard samples and quality control samples are analyzed by concentration calculation with the use of the analysis parameters 201 for a particular analysis item, the reagent information 203, and the calibration curve factor information 204 that is correlated with the reagent information 203

Next, reagent registration will be described.

A reagent bar code which is stuck on a reagent cassette 16 includes, as reagent information, the reagent production lot number, reagent expiration date, and sequence number of a reagent. The sequence number is uniquely assigned to the reagent cassette. Each reagent cassette can be identified by its sequence number.

Registration of the reagent cassette 16 starts with loading it into a reagent cassette slot 18. After detecting the loaded reagent cassette, a reagent bar-code reader 17 reads its reagent bar code. By using as keys the reagent code, the reagent production lot number, and the sequence number that are included in the read reagent bar code, the controller 20 searches the reagent information 203 that has been formerly registered for any reagent with those pieces of information. If the controller 20 does not find any, it judges that the reagent included in the reagent cassette 16 is a new one. In that case, the reagent vessel opening mechanism 12 opens a reagent bottle in the reagent cassette 16, and the reagent cassette transfer mechanism 14 then transfers the reagent cassette to a vacant position on the reagent disk 15.

At this time, the controller 20 searches, with the use of the reagent code of the transferred regent cassette as a search key, for any relevant analysis item from among the analysis items whose analysis parameters have already been registered. Further, the controller 20 stores the reagent unsealing time on the hard disk as the reagent information 203 for that reagent cassette, along with the reagent code, reagent production lot number, sequence number, reagent expiration date, analysis item code, etc.

Even in the case of an automatic analyzer without a reagent vessel opening mechanism, a new reagent vessel is usually opened immediately before its new reagent is registered in the automatic analyzer. Therefore, if it is judged that the registered reagent is new, the registration time of the reagent can be regarded as the reagent unsealing time.

According to this preferred embodiment, the calibration curve factor is input from a screen. Alternatively, the calibration curve factor may be input through an external medium or a network or may be created based on calibration measurement. FIG. 3 is a diagram illustrating a calibration curve factor input/display screen.

A calibration curve factor information table 301 shows calibration curve factors 304 for their respective reagents used for respective analysis items. For calibration curve factor columns A through D, effective factors are determined by a calibration curve type defined on an analysis item basis. For example, "Test1" is a type that requires two factors A and B. Calibration curve factors are updated by inputting different factor values into corresponding cells in the calibration curve factor columns A through D and then by clicking a "Register" button 303. Reference numeral 302 represents a cancel button.

Next, calibration curve factor update processing will be described with reference to a flowchart.

Figure 4:
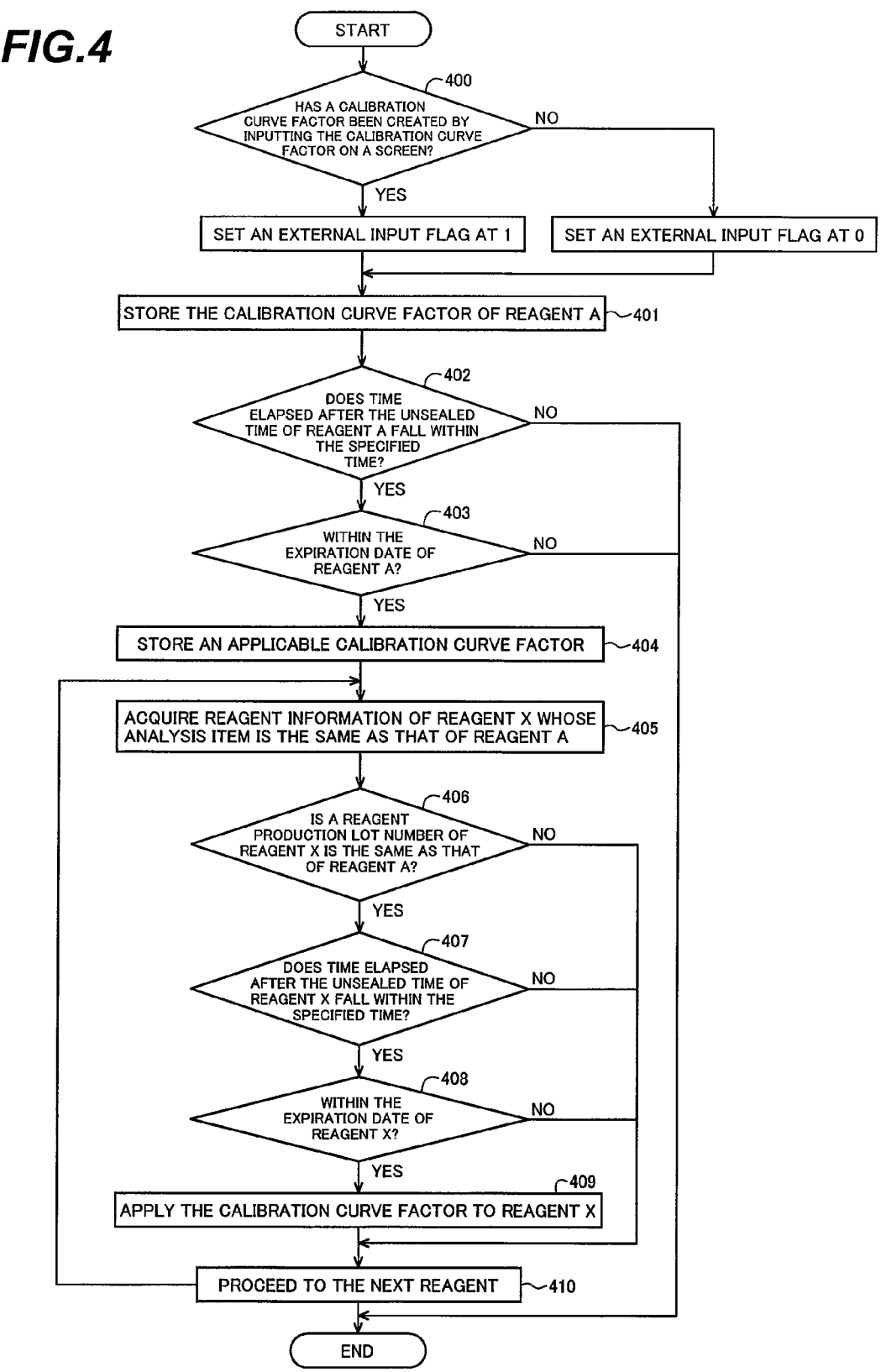
FIG. 4 is a flowchart illustrating processing of applying a calibration curve factor to other reagents.

FIG. 4 is a flowchart illustrating processing of applying a calibration curve factor inputted for a reagent A to another reagent (reagent X).

In step 400, a judgment is made as to whether a calibration curve factor has been created by inputting the calibration curve factor on a screen or on the basis of measurement. If it is judged that the calibration curve factor has been created by the screen input, an external input flag is set at 1. If it is judged that the calibration curve factor has been created on the basis of measurement, an external input flag is set at 0.

In step 401, the calibration curve factor and the external input flag are stored as the calibration curve factor information 204.

In step 402, a judgment is made as to whether or not the time from the unsealing of the reagent A up to the time at which the calibration curve factor has been inputted falls within the specified time that has been set as the analysis parameter 201.

In step 403, a judgment is made as to whether or not the expiration date of the reagent A remains.

If the conditions of the steps 402, 403 are satisfied, it is judged that the inputted calibration curve factor can be applied. Accordingly, the inputted calibration curve factor, and the external input flag that has been set as described above are stored as the applicable calibration curve factor information 202 (step 404). If the conditions of the steps 402, 403 are not satisfied, it is judged that the calibration curve factor has been inputted for a deteriorated reagent. Therefore, the processing ends without applying the calibration curve factor to another reagent.

If it is judged that the calibration curve factor is applicable, then processing of applying the calibration curve factor to another reagent is performed.

A registered reagent X on a reagent disk is compared with the reagent A corresponding to the calibration curve factor that has been judged to be applicable.

In step 405, reagent information of the reagent X whose analysis item is the same as that of the reagent A is acquired.

In step 406, a judgment is made as to whether or not a reagent production lot number of the reagent X is the same as that of the reagent A.

In step 407, a judgment is made as to whether or not the time elapsed after the unsealing of the reagent X falls within the specified time.

In step 408, a judgment is made as to whether or not the expiration date of the reagent X remains.

If all of the conditions of the steps 406 through 408 are satisfied, the inputted calibration curve factor becomes applicable (step 409). Accordingly, the calibration curve factor in question is stored as calibration curve factor information 204 of the reagent X.

If the conditions of the steps 406 through 408 are not completely satisfied, it is judged that the reagent X differs in nature from the reagent A corresponding to the inputted calibration curve factor. Therefore, the inputted calibration curve factor is not applied.

After calibration curve factors are inputted, values of applied factors A through D are displayed in the list of the calibration curve factors 202 shown in FIG. 2 according to the calibration curve factor information 204. If a value of the external input flag of the calibration curve factor information 204 is 1, "*" is displayed in an input field 304. This informs an operator that a calibration curve factor which has been inputted from the outside is applied.

Therefore, when something is wrong with the accuracy control data as a result of the sample analysis thereafter, it is possible to quickly judge whether or not the wrong data is caused by an external input error of a calibration curve factor.

Figure 5:
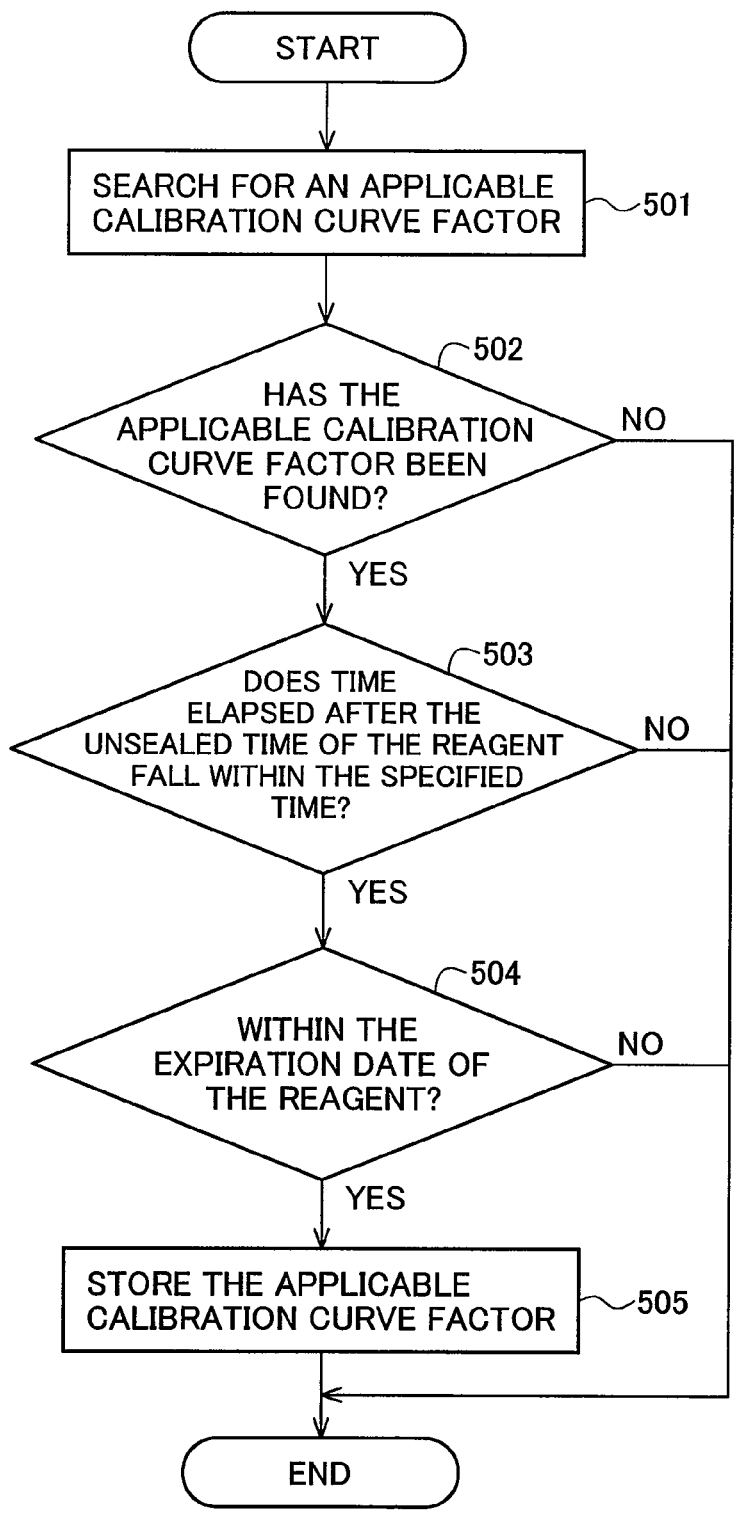
FIG. 5 is a flowchart illustrating processing of applying a calibration curve factor at the time of reagent registration.

FIG. 5 is a flowchart illustrating the processing of applying a calibration curve factor at the time of reagent registration.

In step 501, after a reagent is registered, the applicable calibration curve factor information 202 is searched for by using as keys an analysis item code, a reagent code, and a reagent lot number, corresponding to the registered reagent.

In step 502, a judgment is made as to whether or not the applicable calibration curve factor information 202 which satisfies the above search conditions has been found.

In step 503, a judgment is made as to whether or not the time that elapsed after the opening of the reagent vessel up to the registration of the reagent falls within a specified time.

In step 504, a judgment is made as to whether or not the expiration date of the registered reagent remains.

If all of the conditions of the steps 502 through 504 are satisfied, an applicable calibration curve factor is stored as the calibration curve factor information 204 of the registered reagent (step 505).

If all of the conditions of the steps 502 through 504 are satisfied, the calibration curve factor which has been found is recorded in the calibration curve factor information 204 as a calibration curve factor for the reagent in question.

It is needless to say that if an automatic analyzer constituted of a plurality of analysis modules separately manages a calibration curve factor on an analysis module basis, application of the calibration curve factor can be limited within an analysis module by adding an analysis module number to key information of the calibration curve factor information 204, and to that of the applicable calibration curve factor information 202.

In the above embodiment, the calibration curve factor was described as an example of information about a calibration curve. However, other information may also be used so long as each calibration curve can be identified by the information. For example, an identification number may also be given to each calibration curve so that each calibration curve can be identified by the identification number.

In addition, a judgment as to whether or not a reagent is effective is made by comparing the elapsed time after the reagent is opened with a predetermined threshold value, and further by checking whether or not the expiration date of the reagent remains so as to evaluate a change (deterioration) in characteristics of the reagent. However, instead of making such an ON/OFF judgment, other methods may also be employed. For example, the elapsed time after the opening, the remaining expiration date, or the like, is divided into a plurality of stages; and information about a calibration curve corresponding to each stage is stored.

Moreover, a judgment as to whether or not a placed reagent is the same reagent may also be made not only by checking whether or not a production lot of the placed reagent is the same, but also by using information other than the production lot. Further, instead of always using the production lot, calibration curve information, which is stored in response to the elapsed time after the opening, and the remaining time until the expiration of the expiration date, may also be employed after it is judged that the reagent is the same.

In addition, if the same kind of reagent is provided with a plurality of pieces of calibration curve information, calibration curve information obtained last time may also be applied as calibration curve information of a newly placed reagent. Moreover, selection means may also be provided. The selection means allows a user of the automatic analyzer to select whether or not calibration curve information of a reagent, which has been stored in storage means, is stored as calibration curve information of a placed reagent. Further, it may also be so configured that a group of reagents to be applied is registered beforehand, and that if a reagent is judged to have been registered, a stored calibration curve is automatically applied to the reagent, whereas if the reagent is not judged to have been registered, the user is allowed to select whether to apply the stored calibration curve to the reagent or to newly create a calibration curve.

Furthermore, a display screen for allowing a user to select whether or not a calibration curve is applied to a reagent may also be provided. To be more specific, the user can review a display screen that displays information about a calibration curve, and a state of a reagent in which the calibration curve is obtained (the elapsed time after the opening, the expiration date, and the like); and the user can use a button, or the like, on the display screen to select whether or not to apply the calibration curve.

What is claimed is:

1. An automatic analyzer comprising:
   a storage unit for storing, on a reagent-by-reagent basis, calibration curve information; and
   a controller configured to judge, when a reagent set is newly provided for the automatic analyzer, whether or not the calibration curve information of another reagent set for a same analysis item as the newly provided reagent set has already been stored in the storage unit, and whether or not said another reagent set whose calibration curve information has already been stored is effective;
   wherein the storage unit stores a result of judgment as to whether or not said another reagent set is effective;
   wherein if the calibration curve information of said another reagent set for the same analysis item as the newly provided reagent set has already been stored in the storage unit, and if said another reagent set is effective, the controller stores in the storage unit the calibration curve information of said another reagent set as the calibration curve information of the newly provided reagent set into the storage unit;

wherein if the controller judges that the calibration curve information of said another reagent set for the same analysis item as the newly provided reagent set has been stored in the storage unit but said another reagent set is not effective, the controller creates a calibration curve of the reagent set which is newly provided for the automatic analyzer;

wherein said controller stores in the storage unit the calibration curve information of the calibration curve created for the newly provided reagent set, independent of the calibration curve information already stored in the storage unit; and wherein the calibration curve information is a calibration curve factor used to identify a calibration curve.

2. The automatic analyzer according to claim 1, wherein the result of the judgment as to whether or not said another reagent set is effective, which is to be stored on the storage unit, is a judgment result based on the information including an elapsed time after opening of reagent vessels of said another reagent set and an expiration date of said another reagent set.

3. The automatic analyzer according to claim 1, wherein to judge whether or not the calibration curve information of another reagent set for a same analysis item as the newly provided reagent set has already been stored in the storage unit, by the controller, comprises a judgment as to whether or not said another reagent set and the newly provided reagent set have a same production lot number.

4. The automatic analyzer according to claim 1, wherein the controller stores in the storage unit, the calibration curve information of said another reagent set that has already been stored, as the calibration curve information of the newly provided reagent set only when said another reagent set is judged effective.

5. The automatic analyzer according to claim 1, wherein the calibration curve information of said another reagent set which is stored in the storage unit is a latest calibration curve information of said another reagent set.

6. The automatic analyzer according to claim 1, further comprising a display screen for allowing a user to review calibration curve information stored in the storage unit.

7. The automatic analyzer according to claim 1, further comprising a display screen for allowing a user to update calibration curve factors for reagents used for analysis item.

8. The automatic analyzer according to claim 1, wherein said another reagent set for the same analysis item and the newly provided reagent set have same production lot number.

9. The automatic analyzer according to claim 1, wherein if the controller judges that the calibration curve information of said another reagent set for the same analysis item as the newly provided reagent set has not been stored in the storage unit, the controller creates a calibration curve of the reagent set which is newly provided for the automatic analyzer.

* * * * *